(12) United States Patent
Obara et al.

(10) Patent No.: US 9,784,751 B2
(45) Date of Patent: Oct. 10, 2017

(54) METHOD FOR DETECTING NEUROLOGICAL DISEASE ASSOCIATED WITH COGNITIVE IMPAIRMENT BY MEASURING EPHA4 EXTRACELLULAR DOMAIN

(75) Inventors: Takashi Obara, Tsukuba (JP); Eiji Inoue, Kobe (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 14/113,385

(22) PCT Filed: Apr. 25, 2012

(86) PCT No.: PCT/JP2012/061097
§ 371 (c)(1),
(2), (4) Date: Dec. 5, 2013

(87) PCT Pub. No.: WO2012/147798
PCT Pub. Date: Nov. 1, 2012

(65) Prior Publication Data
US 2014/0080146 A1  Mar. 20, 2014

(30) Foreign Application Priority Data

Apr. 25, 2011  (JP) .................................. 2011-097377

(51) Int. Cl.
*G01N 33/68* (2006.01)
*C12N 9/12* (2006.01)

(52) U.S. Cl.
CPC ........... *G01N 33/6896* (2013.01); *C12N 9/12* (2013.01); *C12Y 207/10001* (2013.01); *G01N 2800/2814* (2013.01); *G01N 2800/2821* (2013.01)

(58) Field of Classification Search
None
See application file for complete search history.

(56) References Cited

U.S. PATENT DOCUMENTS

| | | | |
|---|---|---|---|
| 5,876,946 A | 3/1999 | Burbaum et al. | |
| 5,902,732 A | 5/1999 | Hochman | |
| 7,892,769 B2 | 2/2011 | Inoue et al. | |
| 7,910,324 B2 | 3/2011 | Inoue | |
| 8,137,926 B2 | 3/2012 | Inoue | |
| 8,530,181 B2 | 9/2013 | Inoue | |
| 2002/0068361 A1 | 6/2002 | Clary | |
| 2004/0180823 A1* | 9/2004 | Pasquale et al. | ............... 514/12 |
| 2006/0241074 A1 | 10/2006 | Woolf et al. | |
| 2007/0015145 A1 | 1/2007 | Woolf et al. | |
| 2007/0026409 A1 | 2/2007 | Woolf et al. | |
| 2007/0253954 A1* | 11/2007 | Nakamura et al. | ........ 424/138.1 |
| 2008/0213250 A1 | 9/2008 | Hopf et al. | |
| 2009/0023158 A1 | 1/2009 | Shapiro et al. | |
| 2009/0142788 A1 | 6/2009 | Inoue | |
| 2009/0163594 A1 | 6/2009 | Shapiro et al. | |
| 2009/0191580 A1 | 7/2009 | Inoue | |
| 2009/0275049 A1 | 11/2009 | Inoue et al. | |
| 2010/0021950 A1 | 1/2010 | Lammert et al. | |
| 2010/0113415 A1 | 5/2010 | Rajapakse et al. | |
| 2010/0166657 A1* | 7/2010 | Kinch et al. | ................... 424/9.1 |
| 2010/0190184 A1 | 7/2010 | Inoue | |
| 2010/0255522 A1 | 10/2010 | Inoue | |
| 2011/0104171 A1 | 5/2011 | Inoue et al. | |
| 2011/0111444 A1 | 5/2011 | Inoue | |
| 2013/0288278 A1* | 10/2013 | Inoue | ........................ 435/7.92 |

FOREIGN PATENT DOCUMENTS

| | | |
|---|---|---|
| EP | 0351585 A2 | 1/1990 |
| EP | 1514925 A1 | 5/2002 |
| EP | 1662259 | 5/2006 |
| EP | 1693449 A1 | 8/2006 |
| EP | 1947193 A1 | 7/2008 |
| EP | 1815255 | 4/2009 |
| EP | 2166110 A1 | 3/2010 |
| EP | 2177623 | 4/2010 |
| EP | 2192181 | 6/2010 |
| EP | 2223999 | 9/2010 |
| EP | 2260864 | 12/2010 |
| EP | 2219028 | 9/2012 |
| JP | 2824433 | 9/1998 |
| JP | 2003-169699 A | 6/2003 |
| JP | 3680114 | 5/2005 |
| JP | 2006-508653 | 3/2006 |
| WO | 98/45708 A1 | 10/1998 |
| WO | 03/016475 A2 | 2/2003 |
| WO | 2004/048578 A1 | 6/2004 |
| WO | 2005/045028 A1 | 5/2005 |
| WO | 2005/083086 | 9/2005 |
| WO | 2006/026820 | 3/2006 |
| WO | 2006/056467 | 6/2006 |
| WO | 2006/061660 | 6/2006 |
| WO | 2008/087035 A2 | 7/2008 |

(Continued)

OTHER PUBLICATIONS

Massimiliano et al, ACS Chem Neurosci 5: 1146-1147, 2014.*
Verbaan et al J Neurol Neurosurg Psychiat 78: 1182-1187, 2007.*
Kayman et al, Curr Tran Geriat Gerontol Rep 1: 45-52, Feb. 2012.*
Simon et al (J Alz Dis 17: 773-786, 2009).*
Noberini et al (JBC 283: 29461-29472, 2008).*
Pagonabarraga et al Neurobiol Dis 46: 590-596, 2012.*
Kwok-On Lai and Nancy Y Ip, "Synapse development and plasticity: roles of ephrin/Eph receptor signaling", Current Opinion in Neurobiology, vol. 19:275-283 (2009).
Response to the European Search Report for corresponding EP Application No. 11848175.3 filed on Jan. 20, 2015.
Response to European Search Report for corresponding EP Application No. 12776929.7 filed May 6, 2015.

(Continued)

*Primary Examiner* — Daniel E Kolker
*Assistant Examiner* — Aditi Dutt
(74) *Attorney, Agent, or Firm* — Fish & Richardson P.C.

(57) ABSTRACT

A method for detecting a neurological disease associated with cognitive impairment, wherein the extracellular domain of EphA4 is measured from a biological sample taken from a subject.

4 Claims, 1 Drawing Sheet

(56) References Cited

FOREIGN PATENT DOCUMENTS

| WO | 2008/150010 A1 | 12/2008 |
|---|---|---|
| WO | 2009/069808 | 6/2009 |

OTHER PUBLICATIONS

Akimoto et al., "Hepatocyte Growth Factor as an Enhancer of NMDA Currents and Synaptic Plasticity in the Hippocampus", Neuroscience; 128(1):155-62 (2004).
Amtul et al., "A Presenilin 1 Mutation Associated with Familial Frontotemporal Dementia Inhibits γ-secretase Cleavage of APP and Notch", Neurobiol. Disease., vol. 9, No. 2, pp. 269-273 (2002).
Aoto, J. and Chen, L., "Bidirectional ephrin/Eph signaling in synaptic functions," Elsevier, Brain Res. (2007) vol. 1184 72-80.
Aoki et al., EphA Receptors Direct the Differentiation of Mammalian Neural Precursor Cells through a Mitogen-activated Protein Kinase-dependent Pathway, J. Biol. Chem. , 2004, vol. 279, No. 31, p. 32643-32650.
Beg et al., "α2-Chimaerin Is an Essential EphA4 Effector in the Assembly of Neuronal Locomotor Circuits", Neuron 55, 768-778, 2007.
Braak and Braak, "Neuropathological stageing of Alzheimer-related changes, Acta". Neuropathol., 82: 239-259 (1991).
Carter, Chris; "Alzheimer's Disease: APP, Gamma Secretase, APOE, CLU, CRI, PICALM, ABCA7, BINI, CD2AP, CD33, EPHAI, and MS4A2, and Their Relationships with Herpes Simplex, C. Pneumoniae, Other Suspect Pathogens, and the Immune System", International J of Alzheimer's Disease vol. 2011, pp. 1-34 (2011).
Cheng et al., "γ-Secretase activity is dispensable for mesenchyme to epithelium transition but required for podocyte and proximal tubule formation in developing mouse kidney", Development, vol. 130, No. 20, pp. 5031-5042 (2003).
Communication for EP08765357.2 dated Feb. 4, 2011.
Consultation by telephone for EP08849729 dated Mar. 20, 2012.
Decision of final rejection for JP2009-543902 dated Aug. 20, 2013 (with English translation).
Dufour et al., "Genetic analysis of EphA-dependent signaling mechanisms controlling topographic mapping in vivo", Development, 133: 4415-4420 (2006).
Eriksen et al, "NSA1Ds and enantiomers of flurbiprofen target Y-secretase and lower Aβ42 in vivo", J, Clin, Invest, 112, 440-449 (2003).
Esumi et al., "Expression of receptor type tyrosine kinase EphA4 in the spinal cord of autopsy and normal cases", Shinkei Hensei Shikkan ni Kansuru Kenkyuhan 2000 Nendo Kenkyu, Hokokusho, 2001, pp. 48 to 50.
Ethell and Ethell, "Matrix Metalloproteinases in Brain Development and Remodeling: Synaptic Functions and Targets", J Neurosci Res., 85(13):2813-23 (2007).
European Search Report EP08849729 dated Nov. 26, 2010.
European Search Report EP08765357 dated Jun. 25, 2010.
European Search Report EP08791346 dated Nov. 29, 2010.
European Search Report EP088536263 dated Apr. 4, 2011.
Extended Search Report for EP Application No. 08792114.4 dated Nov. 9, 2010.
Extended Search Report for EP Application No. 11848175.3 dated Jul. 21, 2014.
Final Office Action for U.S. Appl. No. 12/175,595 dated Nov. 8, 2011.
Folstein et al., "Mini-Mental State" A Practical Method for Grading the Cognitive State of Patients for the Clinician, J Psychiatr Res 12: 189-198 (1975).
Foveau et al., "Down-Regulation of the Met Receptor Tyrosine Kinase by Presenilin-Dependent Regulated Intramembrane Proteolysis", Molecular Biology of the Cell, vol. 20, 2495-2507 (2009).
Fox et al., cDNA cloning and tissue distribution of five human EPH-like receptor protein-tyrosine kinase's, Oncogene(1995) vol. 10, No. 5 897-905.
Fraering et al. "γ-Secretase Substrate Selectivity Can Be Modulated Directly via Interaction with a Nucleotide-binding Site", Journal of Biological Chemistry 280(51) 41987-41996 (2005).
Gähwiler, B, H, "Organotypic cultures of neural tissue", Trends Neurosci. 11(11): 484-489 (1988).
Galasko et al., "An Inventory to Assess Activities of Daily Living for Clinical Trials in Alzheimer's Disease", Alzheimer Dis Assoc Disord, 11 suppl 2: S33-9 (1997).
Georgakopoulos et al., "Metalloproteinase/Presenilin 1 processing of ephrinB regulates EphB-induced Src phosphorylation and signaling", The EMBO Journal, vol. 25, p. 1242-1252 (2006).
Haapasalo et al, "Presenilin/γ-Secretase-mediated Clevage Regulates Association of Leukocyte-Common Antigen-related (LAR) Receptor Tyrosine Phosphatase with β-Catenin", J. Biol. Chem, American Society for Biochem, and Molecular Biology Inc.US, vol. 282 No. 12 pp. 9063-9072 (2007).
Hansson et al., "Nicastrin, Presenilin, APH-I, and PEN-2 Form Active γ-Secretase Complexes in Mitochondria", J, Biol. Chem; vol. 279, Issue 49, 51654-51660 (2004).
Hering and Sheng, Dendritic Spines: Structure, Dynamics and Regulation, Nat. Rev. Neurosci. 2(12):880-8 (2001).
Hitoshi et al., "Efficient selection for high-expression transfectants with a novel eukaryotic vector", Gene. 108: 193-200 (1991).
Holmberg et al., "Regulation of repulsion versus adhesion by different splice forms of an Eph receptor", Nature, vol. 408, No. 6809, p. 203-206 (2000).
Houston and Banks, "The chemical-biological interface: developments in automated and miniaturised screening technology", Curr Opin. Biotechnol, 8, pp. 734-740 (1997).
Inoue et al., Synaptic activity prompts γ-secretase-mediated, clevage of EphA4 and dendritic spine formation, J. Cell Biol. vol. 185 No. 3, p. 551-564, 2009.
Inoue et al., "Alzheimer's Disease (AD), No ni Okeru EphA4/gamma-secretase Signal no Henka", Dement. Jpn., Nov. 15, 2011 (Oct. 15, 2011), vol. 25, No. 3, p. 339.
International Search Report for PCT/JP2008/060567 dated Aug. 26, 2008.
International Search Report for PCT/JP2008/063037 dated Sep. 9, 2008.
International Search Report for PCT/JP2008/063901 dated Aug. 26, 2008.
International Search Report for PCT/JP2008/070864 dated Jan. 6, 2009.
International Search Report for PCT/JP2008/071831 dated Jan. 27, 2009.
International Search Report for PCT/JP2011/078460 dated Jan. 10, 2012.
International Search Report for PCT/JP2012/061097 dated Aug. 7, 2012.
Invitrogen product sheet for "Mouse anti-EphA4 Receptor", Downloaded from web on Apr. 5, 2013.
Jayawickreme and Kost, "Gene expression systems in the development of high-throughput screens", Curr Opin. Biotechnol., 8, pp. 629-634 (1997).
Kaether et al., "Assembly, trafficking and function of gamma-secretase.", Neurodegener Dis. 3(4-5):275-83 (2006).
Kawarabayashi et al., "Age-Dependent Changes in Brain, CSF, and Plasma Amyloid β Protein in the Tg2576 Transgenic Mouse Model of Alzheimer's Disease", J, Neurosci. 21(2), 372-381 (2001).
Khachaturian, Z., "Diagnosis of Alzheimer's Disease", Arch Neuro 42: 1097-1105 (1985).
Koehler and Milstein, "Continuous cultures of fused cells secreting antibody of predefined specificity", Nature, 256, 495 (1975).
Kopan, R. and Ilagan, M. X.., "γ-Secretase: proteasome of the membrane?", Nature Reviews Molecular Cell Biology, 6, vol. 5, p. 499-504 (2004).
Kuure et al., "Crosstalk between Jabbed1 and GDNF/Ret/GFRα1 signalling regulates ureteric budding and branching", Mech, Dev, vol. 122, No. 6, pp. 765-780 (2005).

(56) References Cited

OTHER PUBLICATIONS

Landman, N. and Kim, T. et al., Got RIP? Presenilin-dependent intramembrane proteolysis in growth factor receptor signaling, Cytokine & Growth Factor Reviews, vol. 15, pp. 337-351 (2004).
Lanz et al., "The γ-Secretase Inhibitor N-[N-(3,5-Difluorophenacetyl)-L-alanyl]-S-phenylglycine t-butyl Ester Reduces Aβ Levels in Vivo in Plasma and Cerebrospinal Fluid in Young (Plaque-Free) and Aged (Plaque-Bearing) Tg2576 Mice", Pharmacol. Exp, Ther, vol. 305, No. 3; 864-871 (2003).
Lee et al., "Presenilin-dependent γ-Secretase-like Intramembrane Cleavage of ErbB4*", The Journal of Biological Chemistry, vol. 277, pp. 6318-6323 (2002).
Lin et al., "Ephrin-B2-induced Cleavage of EphB2 Receptor Is Mediated by Matrix Metalloproteinases to Trigger Cell Repulsion", J. of Biol. Chem. , 283(43):28969-28979 (2008).
Litterst et al., "Ligand Binding and Calcium Influx Induce Distinct Ectodomain/ γ-Secretase-processing Pathways of EphB2 Receptor", J. Biol Chem, vol. 282, No. 22, pp. 16155-16163 (2007).
Liu et al., "Intramembrane Proteolysis of human NotchdeltaE", Society of Neuroscience, Abstract Viewer and Itinerary Planner, vol. 2003 pp. Abstract No. 729.11 (2003).
Maretzky, Thorsten et al., L1 Is Sequentially Processed by Two Differently Activated Metalloproteases and Presenilin/γ-Secretase and Regulates Neural Cell Adhesion, Cell Migration, and Neurite Outgrowth, Molecular and Cellular Biology, p. 9040-9053 vol. 25, No. 20 (2005).
Martone et al., "Immunolocalization of the receptor tyrosine kinase EphA4 in the adult rat central nervous system", Brain Research , 771: 238-250 (1997).
Maulik et al., "Role of the hepatocyte growth factor receptor, c-Met, in oncogenesis and potential for therapeutic inhibition", Cytokine Growth Factor Rev, 13(1):41-59 (2002).
McKhann et al, Clinical diagnosis of Alzheimer's disease: Report of the NINCDS-ADRDA Work Group* under the auspices of Department of Health and Human Services Task Force on Alzheimer's Disease, Neurology 34: 939-944 (1984).
McLendon et al. "Cell-free assays for γ-secretase activity[1]", The FASEB Journal 14: 2383-2386 (2000).
Minopoli et al., "Receptor-and Non-Receptor Tyrosine Kinases Induce Processing of the Amyloid Precursor Protein: Role of the low-Density lipoprotein Receptor-Related Protein", Neurodegener Dis., vol. 4, No. 2-3, pp. 94-100 (2007).
Mirra et al, "Making the Diagnosis of Alzheimer's Disease. A Primer for Practicing Pathologists", Arch Pathol Lab Med 117: 132-144 (1993).
Mirra et al., The Consortium to Establish a Registry for Alzheimer's Disease (CERAD). Part II. Standardization of the neuropathologic assessment of Alzheimer's disease, Neurology 41: 479-486 (1991).
Moehlmann et al. "Presenilin-1 mutations of leucine 166 equally affect the generation of the Notch and APP intracellular domains independent of their effect on $A\beta_{42}$ production", PNAS 99(12): 8025-8030 (2002).
Mohs., "*Comprehensive and Neuropsychologic Evaluations*, The Alzheimer's Disease Assessment Scale", Int Psychogeriatr 8: 195-203 (1996).
Murai et al., "Control of hippocampal dendritic spine morphology through ephrin-A3/EphA4 signaling", Nat. Neurosci., vol. 6, No. 2, p. 153-160 (2003).
Muramatsu et al., "Gelatinase", from Dictionary of Molecular Cell Biology, eds., Showado Insatsusho 1997) at 457-458 (with English translation).
Murphy et al., "γ-Secretase, Evidence for Multiple Proteolytic Activities and, Influence of membrane Positioning of, Substrate, on Generation of Amyloid β Peptides of Varying Length", J, Biol Chem, vol. 274, No. 17, p. 11914-11923 (1999).
Nakanishi et al., "ALL1 fusion proteins induce deregulation of EphA7 and ERK phosphorylation in human acute leukemias", Proc Natl Acad Sci USA, vol. 104, No. 36, p. 14442-14447 (2007).
Nath et al., "Shedding of c-Met is regulated by crosstalk between a G-protein coupled receptor and the IEGF receptor and is mediated by a TIMP-3 sensitive metalloproteinase", Journal of Cell Science, vol. 114, p. 1213-1220 (2001).
Notice of Allowance for U.S. Appl. No. 12/742,312 dated Nov. 5, 2012.
Notice of Allowance for U.S. Appl. No. 13/993,126 dated Jun. 24, 2014.
Notice of trial and amendment for JP2009-543902 filed on Nov. 19, 2013 (with English translation).
Office Action (Restriction Requirement) U.S. Appl. No. 12/986,922 dated Jan. 18, 2013.
Office Action EP088497292 dated Apr. 26, 2012.
Office Action EP08853626 dated Nov. 18, 2011.
Office Action EP088536263 dated Oct. 29, 2012.
Office Action for EP088536263 dated Aug. 5, 2013.
Office Action JP2009-517923 dated Jul. 2, 2013 (with English translation).
Office Action U.S. Appl. No. 12/135,307 dated Jun. 10, 2010.
Office Action U.S. Appl. No. 12/175,595 dated Apr. 18, 2012.
Office Action U.S. Appl. No. 12/175,595 dated May 17, 2011.
Office Action U.S. Appl. No. 12/325,418 dated Apr. 1, 2010.
Office Action U.S. Appl. No. 12/670,987 dated Dec. 4, 2005.
Office Action U.S. Appl. No. 12/742,312 dated Jul. 17, 2012.
Office Action U.S. Appl. No. 12/986,922 dated Apr. 10, 2013.
Office Action U.S. Appl. No. 13/009,127 dated Jul. 13, 2011.
Office Action U.S. Appl. No. 13/993,126 dated Feb. 28, 2014.
Office Action (Restriction Requirement) U.S. Appl. No. 12/135,307 dated Mar. 19, 2010.
Office Action (Restriction Requirement) U.S. Appl. No. 12/742,312 dated May 14, 2012.
Office Action (Restriction Requirement) U.S. Appl. No. 12/325,418 dated Nov. 10, 2009.
Office Action for JP2009-541201 dated Sep. 24, 2013 (with English translation).
Office Action for JP2009-543902 dated Feb. 28, 2012 (with English translation).
Office Action for JP2009-543902 dated Nov. 6, 2012 (with English translation).
Pak et al., "Regulation of Dendritic Spine Morphology by SPAR, a PSD-95-Associated RapGAP", Neuron 31:289-303 (2001).
Pelletier et al., γ-secretase-Dependent Proteolysis of CD44 Promotes Neoplastic Transformation of Rat Fibroblastic Cells, Cancer Res., vol. 66, No. 7, pp. 3681-3687 (2006).
Penzes et al., "Convergent CaMK and RacGEF signals control dendritic structure and function", Trends in Cell Biol. 18(9):405-413 (2008).
Pozner-Moulis et al., "Met, the Hepatocyte Growth Factor Receptor, Localizes to the Nucleus in Cells at Low Density", Cancer Reseatch, vol. 66, pp. 7976-7982 (2006).
Predicted: Rattus norvegicus similar to Eph receptor A4 (LOC316539), mRNA; NCBI_AccessionNo.XM_244186.3.
Ra, H. and Parks, W., "Control of Matrix Metalloproteinase Catalytic Activity", Matrix Biol .26(8): 587-596 (2007).
Ramakers, Ger J.A., "Rho proteins, mental retardation and the cellular basis of cognition", Trends Neurosci. 25(4):191-9 (2002).
Ray et al., "Evidence for a physical interaction between presenilin and Notch", PNAS, vol. 96, No. 6, p. 3263-3268 (1999).
Request for Continued Examination for U.S. Appl. No. 12/742,312 dated Feb. 5, 2013.
Response to Communication for EP08765357.2 dated Jun. 1, 2011.
Response to EP Office Action for EP08792114.4.-1223 filed May 26, 2011.
Response to Final Office Action U.S. Appl. No. 12/175,595 dated Feb. 8, 2012.
Response to Office Action JP2009-543902 dated Apr. 27, 2012 (with English translation).
Response to Office Action JPA2009-543902 dated Dec. 28, 2012 (with English translation).
Response to Office Action EP08765357 filed Jan. 7, 2011.
Response to Office Action EP08791346.3 filed Jun. 21, 2011.
Response to Office Action EP08849729.2.-1223 filed Jun. 21, 2011.
Response to Office Action EP08853626.3 dated Dec. 11, 2013.

(56) References Cited

OTHER PUBLICATIONS

Response to Office Action EP088536263 dated Mar. 14, 2012.
Response to Office Action EP088536263 dated Dec. 27, 2012.
Response to Office Action EP0885362632405 filed Oct. 21, 2011.
Response to Office Action for JP2009-541201 filed on Nov. 18, 2013 (with English translation).
Response to Office Action JP2009-517923 dated Aug. 29, 2013 (with English translation).
Response to Office Action U.S. Appl. No. 12/135,307 dated May 6, 2010.
Response to Office Action U.S. Appl. No. 12/135,307 dated Sep. 2, 2010.
Response to Office Action U.S. Appl. No. 12/175,595 dated Aug. 18, 2011.
Response to Office Action U.S. Appl. No. 12/325,418 dated Dec. 10, 2009.
Response to Office Action U.S. Appl. No. 12/325,418 dated Jul. 21, 2010.
Response to Office Action U.S. Appl. No. 12/742,312 dated Jun. 11, 2012.
Response to Office Action U.S. Appl. No. 12/742,312 dated Oct. 16, 2012.
Response to Office Action U.S. Appl. No. 12/986,922 dated Feb. 4, 2013.
Response to Office Action U.S. Appl. No. 13/009,127 dated Sep. 28, 2011.
Response to Office Action U.S. Appl. No. 13/993,126 filed Feb. 4, 2014.
Response to Office Action U.S. Appl. No. 13/993,126 filed May 28, 2014.
Sakaguchi et al., "Sprouting of CA3 pyramidal neurons to the dentate gyrus in rat hippocampal organotypic cultures", Neurosci. Res. 20 :157-164 (1994).
Sambrook, et al., Introduction of Recombinant Vectors into Mammalian Cells, Molecular Cloning 3:16.30-16.31 (1989).
Sarlola, H. and M. Saama.,"Novel functions and signalling pathways for GDNF", J, Cell. Sci, vol. 116 pp. 3855-3862 (2003).
Sastre et al., "Presenilin-dependent y-secretase processing of β-amyloid precursor protein at a site corresponding to the S3 cleavage of Notch", Embo Reports, vol. 2, No. 9, p. 835-841 (2001).
Saura, et al., "Loss of Presenilin Function Causes Impairments of Memory and Synaptic Plasticity Followed by Age-Dependent Neurodegeneration", Neuron, vol. 42, No. 1, pp. 23-36 (2004).
Shamah et al., "EphA Receptors Regulate Growth Cone Dynamics through the Novel Guanine Nucleotide Exchange Factor Ephexin", Cell, vol. 105, No. 2, p. 233-244 (2001).
Song et al., "Proteolytic release and nuclear translocation of Notch-1 are induced by presenilin-1 and impaired by pathogenic presenilin-1 mutations", PNAS, 96: 6959-6963 (1999).
Stoppini et al., "A simple method for organotypic cultures of nervous tissue", Neurosci. Methods.37: 173-182 (1991).
Tashiro, A. and Yuste, R. "Regulation of dendritic spine motility and stability by Rac1 and Rho kinase: evidence for two forms of spine motility", Mol Cell Neurosci. 26(3):429-40 (2004).
Tomita et al., "Presenilin-dependent intramembrane cleavage of ephrin-B1", Molecular Neurodegeneration 1 :1-9 (2006).
Tremblay et al., "Localization of EphA4 in Axon Terminals and Dendritic Spines of Adult Rat Hippocampus", Neurol 501: 691-702 (2007).
Tyndall, S. and Walikonis, R. "The Receptor Tyrosine Kinase Met and Its Ligand Hepatocyte Growth Factor are Clustered at Excitatory Synapses and Can Enhance Clustering of Synaptic Proteins", Cell Cycle 5(14):1560-1568 (2006).
Vidal et al., "Presenilin-dependent γ-Secretase Processing Regulates Multiple ERBB4/HERA Activities", Journal of Biological Chemistry, vol. 280, No. 20, p. 19777-19783 (2005).

Wajih et al., "Vascular Origin of a Soluble Truncated Form of the Hepatocyte Growth Factor Receptor (c-met)", Circulation Research 90, 46-52 (2002).
Wikipedia, the free encyclopedia, Gamma secretase; Wikipedia Jan. 16, 2012.
Xu et al., "Expression of truncated Sek-1 receptor tyrosine kinase disrupts the segmental restriction of gene expression in the Xenopus and zebrafish hindbrain", Development, vol. 121, No. 12, p. 4005-4016 (1995).
Yamaguchi, Y. and Pasquale, E.B., "Eph receptors in the adult brain", Current Opinion Neurobiology, 14:288-296, 2004.
Yang, "Preparation and Analysis of Monoclonal Antibody Against EPHA4 Peptide", J.Cent. South Univ.(Med Sci), 30(5):529-532. English translation of original Chinese article; (2005).
Yokote et al., "Trans-activation of EphA4 and FGF receptors mediated by direct interactions between their cytoplasmic domains", PNAS, 102(52):18866-18871 (2005).
Zhao et al., "Role of p21-activated kinase pathway defects in the cognitive deficits of Alzheimer disease", Nat Neurosci. 9(2):234-42 (2006).
Zou et al., "Linking Receptor-mediated Endocytocis and Cell Signalling" Evidence for Regulated Intramembrane Proteolysis of Megalin in Proximal Tubule, J, Biol. Chem , vol. 279, No. 33, pp. 34302-34310 (2004).
"Leading the way to a brighter future", Nature Jobs 2014, Nature 9:505 (7482) (Jan. 2014).
Extended European Search Report for corresponding EP Application No. 12776929.7 dated Nov. 6, 2014.
Office Action issued for European patent application No. 11848175.3 dated Dec. 4, 2015.
Sbai et al., "Vesicular trafficking and secretion of matrix metalloproteinases-2, -9 and tissue inhibitor of metalloproteinases-1 in neuronal cells", Molecular and Cellular Neuroscience, 39(4):549-568 (2008).
Response to Office Action for corresponding JP Application No. 2012-548763, filed on Nov. 5, 2015 (with English translation).
Hardy et al., "The Amyloid Hypothesis of Alzheimer's Disease: Progress and Problems on the Road to Therapeutics", (2002) Science 297(5580):353-56.
Japanese Office Action for JP Application No. 2012-548763 dated Sep. 8, 2015 (with English translation).
Song et al., "Plasma biomarkers for mild cognitive impairment and Alzheimer's disease ", (2009) Brain Res. Dev. 61(2):69-80.
Response to Office Action for Japanese patent application 2012-548763, filed on Jun. 14, 2016, with English translation.
Matsui et al., "Involvement of the γ-Secretase-Mediated EphA4 Signaling Pathway in Synaptic Pathogenesis of Alzheimer's Disease", Brain Pathology, International Society of Neuropathy, pp. 1-12, (2012).
Office Action for Japanese Patent Application No. 2013-512405, dated Mar. 8, 2016.
Response to Office Action for European Patent Application No. 11848175.3, dated Mar. 3, 2016.
Communication issued for European patent application No. 11848175.3 dated Apr. 14, 2016.
Kullander and Klein, "Mechanisms and Functions of EPH and Ephrin Signalling", Nature Reviews, Molecular Cell Biology, 3:475-486 (2002).
Office Action issued for Japanese patent application No. 2012-548763 dated Apr. 19, 2016 (with English translation).
Response to the Office Action for Japanese patent application No. 2013-512405 filed on Apr. 19, 2016 (with English translation).
Office Action in European Patent Application 12776929.7, dated Feb. 27, 2017, 2 pages.
Response to Office Action in European Patent Application 12776929.7, filed Mar. 16, 2017, 16 pages.
Communication issued for corresponding European Application No. 12776929.7 dated May 16, 2017 (32 pages).

* cited by examiner

SEQUENCE LISTING

```
<160> NUMBER OF SEQ ID NOS: 2

<210> SEQ ID NO 1
<211> LENGTH: 986
<212> TYPE: PRT
<213> ORGANISM: Homo sapiens

<400> SEQUENCE: 1

Met Ala Gly Ile Phe Tyr Phe Ala Leu Phe Ser Cys Leu Phe Gly Ile
1               5                   10                  15

Cys Asp Ala Val Thr Gly Ser Arg Val Tyr Pro Ala Asn Glu Val Thr
            20                  25                  30

Leu Leu Asp Ser Arg Ser Val Gln Gly Glu Leu Gly Trp Ile Ala Ser
        35                  40                  45

Pro Leu Glu Gly Gly Trp Glu Glu Val Ser Ile Met Asp Glu Lys Asn
    50                  55                  60

Thr Pro Ile Arg Thr Tyr Gln Val Cys Asn Val Met Glu Pro Ser Gln
65                  70                  75                  80

Asn Asn Trp Leu Arg Thr Asp Trp Ile Thr Arg Glu Gly Ala Gln Arg
                85                  90                  95

Val Tyr Ile Glu Ile Lys Phe Thr Leu Arg Asp Cys Asn Ser Leu Pro
            100                 105                 110

Gly Val Met Gly Thr Cys Lys Glu Thr Phe Asn Leu Tyr Tyr Tyr Glu
        115                 120                 125

Ser Asp Asn Asp Lys Glu Arg Phe Ile Arg Glu Asn Gln Phe Val Lys
    130                 135                 140

Ile Asp Thr Ile Ala Ala Asp Glu Ser Phe Thr Gln Val Asp Ile Gly
145                 150                 155                 160

Asp Arg Ile Met Lys Leu Asn Thr Glu Ile Arg Asp Val Gly Pro Leu
                165                 170                 175

Ser Lys Lys Gly Phe Tyr Leu Ala Phe Gln Asp Val Gly Ala Cys Ile
            180                 185                 190

Ala Leu Val Ser Val Arg Val Phe Tyr Lys Lys Cys Pro Leu Thr Val
        195                 200                 205

Arg Asn Leu Ala Gln Phe Pro Asp Thr Ile Thr Gly Ala Asp Thr Ser
    210                 215                 220

Ser Leu Val Glu Val Arg Gly Ser Cys Val Asn Asn Ser Glu Glu Lys
225                 230                 235                 240

Asp Val Pro Lys Met Tyr Cys Gly Ala Asp Gly Glu Trp Leu Val Pro
                245                 250                 255

Ile Gly Asn Cys Leu Cys Asn Ala Gly His Glu Glu Arg Ser Gly Glu
            260                 265                 270

Cys Gln Ala Cys Lys Ile Gly Tyr Tyr Lys Ala Leu Ser Thr Asp Ala
```

-continued

```
                275                 280                 285
Thr Cys Ala Lys Cys Pro Pro His Ser Tyr Ser Val Trp Glu Gly Ala
290                 295                 300

Thr Ser Cys Thr Cys Asp Arg Gly Phe Phe Arg Ala Asp Asn Asp Ala
305                 310                 315                 320

Ala Ser Met Pro Cys Thr Arg Pro Pro Ser Ala Pro Leu Asn Leu Ile
                325                 330                 335

Ser Asn Val Asn Glu Thr Ser Val Asn Leu Glu Trp Ser Ser Pro Gln
                340                 345                 350

Asn Thr Gly Gly Arg Gln Asp Ile Ser Tyr Asn Val Val Cys Lys Lys
                355                 360                 365

Cys Gly Ala Gly Asp Pro Ser Lys Cys Arg Pro Cys Gly Ser Gly Val
370                 375                 380

His Tyr Thr Pro Gln Gln Asn Gly Leu Lys Thr Thr Lys Val Ser Ile
385                 390                 395                 400

Thr Asp Leu Leu Ala His Thr Asn Tyr Thr Phe Glu Ile Trp Ala Val
                405                 410                 415

Asn Gly Val Ser Lys Tyr Asn Pro Asn Pro Asp Gln Ser Val Ser Val
                420                 425                 430

Thr Val Thr Thr Asn Gln Ala Ala Pro Ser Ser Ile Ala Leu Val Gln
                435                 440                 445

Ala Lys Glu Val Thr Arg Tyr Ser Val Ala Leu Ala Trp Leu Glu Pro
450                 455                 460

Asp Arg Pro Asn Gly Val Ile Leu Glu Tyr Glu Val Lys Tyr Tyr Glu
465                 470                 475                 480

Lys Asp Gln Asn Glu Arg Ser Tyr Arg Ile Val Arg Thr Ala Ala Arg
                485                 490                 495

Asn Thr Asp Ile Lys Gly Leu Asn Pro Leu Thr Ser Tyr Val Phe His
                500                 505                 510

Val Arg Ala Arg Thr Ala Ala Gly Tyr Gly Asp Phe Ser Glu Pro Leu
                515                 520                 525

Glu Val Thr Thr Asn Thr Val Pro Ser Arg Ile Ile Gly Asp Gly Ala
                530                 535                 540

Asn Ser Thr Val Leu Leu Val Ser Val Ser Gly Ser Val Val Leu Val
545                 550                 555                 560

Val Ile Leu Ile Ala Ala Phe Val Ile Ser Arg Arg Arg Ser Lys Tyr
                565                 570                 575

Ser Lys Ala Lys Gln Glu Ala Asp Glu Glu Lys His Leu Asn Gln Gly
                580                 585                 590

Val Arg Thr Tyr Val Asp Pro Phe Thr Tyr Glu Asp Pro Asn Gln Ala
                595                 600                 605

Val Arg Glu Phe Ala Lys Glu Ile Asp Ala Ser Cys Ile Lys Ile Glu
                610                 615                 620

Lys Val Ile Gly Val Gly Glu Phe Gly Glu Val Cys Ser Gly Arg Leu
625                 630                 635                 640

Lys Val Pro Gly Lys Arg Glu Ile Cys Val Ala Ile Lys Thr Leu Lys
                645                 650                 655

Ala Gly Tyr Thr Asp Lys Gln Arg Arg Asp Phe Leu Ser Glu Ala Ser
                660                 665                 670

Ile Met Gly Gln Phe Asp His Pro Asn Ile Ile His Leu Glu Gly Val
                675                 680                 685

Val Thr Lys Cys Lys Pro Val Met Ile Ile Thr Glu Tyr Met Glu Asn
                690                 695                 700
```

Gly Ser Leu Asp Ala Phe Leu Arg Lys Asn Asp Gly Arg Phe Thr Val
705                 710                 715                 720

Ile Gln Leu Val Gly Met Leu Arg Gly Ile Gly Ser Gly Met Lys Tyr
                725                 730                 735

Leu Ser Asp Met Ser Tyr Val His Arg Asp Leu Ala Ala Arg Asn Ile
                740                 745                 750

Leu Val Asn Ser Asn Leu Val Cys Lys Val Ser Asp Phe Gly Met Ser
            755                 760                 765

Arg Val Leu Glu Asp Asp Pro Glu Ala Ala Tyr Thr Thr Arg Gly Gly
770                 775                 780

Lys Ile Pro Ile Arg Trp Thr Ala Pro Glu Ala Ile Ala Tyr Arg Lys
785                 790                 795                 800

Phe Thr Ser Ala Ser Asp Val Trp Ser Tyr Gly Ile Val Met Trp Glu
                805                 810                 815

Val Met Ser Tyr Gly Glu Arg Pro Tyr Trp Asp Met Ser Asn Gln Asp
                820                 825                 830

Val Ile Lys Ala Ile Glu Glu Gly Tyr Arg Leu Pro Pro Pro Met Asp
            835                 840                 845

Cys Pro Ile Ala Leu His Gln Leu Met Leu Asp Cys Trp Gln Lys Glu
850                 855                 860

Arg Ser Asp Arg Pro Lys Phe Gly Gln Ile Val Asn Met Leu Asp Lys
865                 870                 875                 880

Leu Ile Arg Asn Pro Asn Ser Leu Lys Arg Thr Gly Thr Glu Ser Ser
                885                 890                 895

Arg Pro Asn Thr Ala Leu Leu Asp Pro Ser Ser Pro Glu Phe Ser Ala
                900                 905                 910

Val Val Ser Val Gly Asp Trp Leu Gln Ala Ile Lys Met Asp Arg Tyr
            915                 920                 925

Lys Asp Asn Phe Thr Ala Ala Gly Tyr Thr Thr Leu Glu Ala Val Val
930                 935                 940

His Val Asn Gln Glu Asp Leu Ala Arg Ile Gly Ile Thr Ala Ile Thr
945                 950                 955                 960

His Gln Asn Lys Ile Leu Ser Ser Val Gln Ala Met Arg Thr Gln Met
                965                 970                 975

Gln Gln Met His Gly Arg Met Val Pro Val
            980                 985

<210> SEQ ID NO 2
<211> LENGTH: 949
<212> TYPE: PRT
<213> ORGANISM: Homo sapiens

<400> SEQUENCE: 2

Met Ala Gly Ile Phe Tyr Phe Ala Leu Phe Ser Cys Leu Phe Gly Ile
1               5                   10                  15

Cys Asp Ala Val Thr Gly Ser Arg Val Tyr Pro Ala Asn Glu Val Thr
                20                  25                  30

Leu Leu Asp Ser Arg Ser Val Gln Gly Glu Leu Gly Trp Ile Ala Ser
            35                  40                  45

Pro Leu Glu Gly Gly Trp Glu Glu Val Ser Ile Met Asp Glu Lys Asn
        50                  55                  60

Thr Pro Ile Arg Thr Tyr Gln Val Cys Asn Val Met Glu Pro Ser Gln
65                  70                  75                  80

Asn Asn Trp Leu Arg Thr Asp Trp Ile Thr Arg Glu Gly Ala Gln Arg

-continued

```
                        85                  90                  95
Val Tyr Ile Glu Ile Lys Phe Thr Leu Arg Asp Cys Asn Ser Leu Pro
                100                 105                 110

Gly Val Met Gly Thr Cys Lys Glu Thr Phe Asn Leu Tyr Tyr Tyr Glu
            115                 120                 125

Ser Asp Asn Asp Lys Glu Arg Phe Ile Arg Glu Asn Gln Phe Val Lys
        130                 135                 140

Ile Asp Thr Ile Ala Ala Asp Glu Ser Phe Thr Gln Val Asp Ile Gly
145                 150                 155                 160

Asp Arg Ile Met Lys Leu Asn Thr Glu Ile Arg Asp Val Gly Pro Leu
                165                 170                 175

Ser Lys Lys Gly Phe Tyr Leu Ala Phe Gln Asp Val Gly Ala Cys Ile
            180                 185                 190

Ala Leu Val Ser Val Arg Val Phe Tyr Lys Lys Cys Pro Leu Thr Val
        195                 200                 205

Arg Asn Leu Ala Gln Phe Pro Asp Thr Ile Thr Gly Ala Asp Thr Ser
    210                 215                 220

Ser Leu Val Glu Val Arg Gly Ser Cys Val Asn Asn Ser Glu Glu Lys
225                 230                 235                 240

Asp Val Pro Lys Met Tyr Cys Gly Ala Asp Gly Glu Trp Leu Val Pro
                245                 250                 255

Ile Gly Asn Cys Leu Cys Asn Ala Gly His Glu Glu Arg Ser Gly Glu
            260                 265                 270

Cys Gln Ala Cys Lys Ile Gly Tyr Tyr Lys Ala Leu Ser Thr Asp Ala
        275                 280                 285

Thr Cys Ala Lys Cys Pro Pro His Ser Tyr Ser Val Trp Glu Gly Ala
    290                 295                 300

Thr Ser Cys Thr Cys Asp Arg Gly Phe Phe Arg Ala Asp Asn Asp Ala
305                 310                 315                 320

Ala Ser Met Pro Cys Thr Arg Pro Pro Ser Ala Pro Leu Asn Leu Ile
                325                 330                 335

Ser Asn Val Asn Glu Thr Ser Val Asn Leu Glu Trp Ser Ser Pro Gln
            340                 345                 350

Asn Thr Gly Gly Arg Gln Asp Ile Ser Tyr Asn Val Val Cys Lys Lys
        355                 360                 365

Cys Gly Ala Gly Asp Pro Ser Lys Cys Arg Pro Cys Gly Ser Gly Val
    370                 375                 380

His Tyr Thr Pro Gln Gln Asn Gly Leu Lys Thr Thr Lys Val Ser Ile
385                 390                 395                 400

Thr Asp Leu Leu Ala His Thr Asn Tyr Thr Phe Glu Ile Trp Ala Val
                405                 410                 415

Asn Gly Val Ser Lys Tyr Asn Pro Asn Pro Asp Gln Ser Val Ser Val
            420                 425                 430

Thr Val Thr Thr Asn Gln Ala Ala Pro Ser Ser Ile Ala Leu Val Gln
        435                 440                 445

Ala Lys Glu Val Thr Arg Tyr Ser Val Ala Leu Ala Trp Leu Glu Pro
    450                 455                 460

Asp Arg Pro Asn Gly Val Ile Leu Glu Tyr Glu Val Lys Tyr Tyr Glu
465                 470                 475                 480

Lys Asp Gln Asn Glu Arg Ser Tyr Arg Ile Val Arg Thr Ala Ala Arg
                485                 490                 495

Asn Thr Asp Ile Lys Gly Leu Asn Pro Leu Thr Ser Tyr Val Phe His
            500                 505                 510
```

```
Val Arg Ala Arg Thr Ala Ala Gly Tyr Gly Asp Phe Ser Glu Pro Leu
        515                 520                 525
Glu Val Thr Thr Asn Thr Val Pro Ser Arg Ile Ile Gly Asp Gly Ala
        530                 535                 540
Asn Ser Thr Val Leu Leu Val Ser Val Ser Gly Ser Val Val Leu Val
545                 550                 555                 560
Val Ile Leu Ile Ala Ala Phe Val Ile Ser Arg Arg Arg Ser Lys Tyr
                565                 570                 575
Ser Lys Ala Lys Gln Glu Ala Asp Glu Glu Lys His Leu Asn Gln Gly
            580                 585                 590
Val Arg Thr Tyr Val Asp Pro Phe Thr Tyr Glu Asp Pro Asn Gln Ala
        595                 600                 605
Val Arg Glu Phe Ala Lys Glu Ile Asp Ala Ser Cys Ile Lys Ile Glu
        610                 615                 620
Lys Val Ile Gly Val Gly Glu Phe Gly Glu Val Cys Ser Gly Arg Leu
625                 630                 635                 640
Lys Val Pro Gly Lys Arg Glu Ile Cys Val Ala Ile Lys Thr Leu Lys
                645                 650                 655
Ala Gly Tyr Thr Asp Lys Gln Arg Arg Asp Phe Leu Ser Glu Ala Ser
            660                 665                 670
Ile Met Gly Gln Phe Asp His Pro Asn Ile Ile His Leu Glu Gly Val
        675                 680                 685
Val Thr Lys Cys Lys Pro Val Met Ile Ile Thr Glu Tyr Met Glu Asn
        690                 695                 700
Gly Ser Leu Asp Ala Phe Leu Arg Lys Asn Asp Gly Arg Phe Thr Val
705                 710                 715                 720
Ile Gln Leu Val Gly Met Leu Arg Gly Ile Gly Ser Gly Met Lys Tyr
                725                 730                 735
Leu Ser Asp Met Ser Tyr Val His Arg Asp Leu Ala Ala Arg Asn Ile
            740                 745                 750
Leu Val Asn Ser Asn Leu Val Cys Lys Val Ser Asp Phe Gly Met Ser
        755                 760                 765
Arg Val Leu Glu Asp Asp Pro Glu Ala Ala Tyr Thr Thr Arg Gly Gly
        770                 775                 780
Lys Ile Pro Ile Arg Trp Thr Ala Pro Glu Ala Ile Ala Tyr Arg Lys
785                 790                 795                 800
Phe Thr Ser Ala Ser Asp Val Trp Ser Tyr Gly Ile Val Met Trp Glu
                805                 810                 815
Val Met Ser Tyr Gly Glu Arg Pro Tyr Trp Asp Met Ser Asn Gln Asp
            820                 825                 830
Val Ile Lys Ala Ile Glu Glu Gly Tyr Arg Leu Pro Pro Pro Met Asp
        835                 840                 845
Cys Pro Ile Ala Leu His Gln Leu Met Leu Asp Cys Trp Gln Lys Glu
850                 855                 860
Arg Ser Asp Arg Pro Lys Phe Gly Gln Ile Val Asn Met Leu Asp Lys
865                 870                 875                 880
Leu Ile Arg Asn Pro Asn Ser Leu Lys Arg Thr Gly Thr Glu Ser Ser
                885                 890                 895
Arg Pro Asn Thr Ala Leu Leu Asp Pro Ser Ser Pro Glu Phe Ser Ala
            900                 905                 910
Val Val Ser Val Gly Asp Trp Leu Gln Val Ile Lys Met Asp Arg Tyr
        915                 920                 925
```

```
Lys Asp Asn Phe Thr Ala Ala Gly Tyr Thr Thr Leu Glu Ala Val Val
    930                 935                 940
His Val Asn Gln Glu
945
```

METHOD FOR DETECTING NEUROLOGICAL DISEASE ASSOCIATED WITH COGNITIVE IMPAIRMENT BY MEASURING EPHA4 EXTRACELLULAR DOMAIN

CROSS-REFERENCE TO RELATED APPLICATIONS

This is the U.S. National Phase, submitted pursuant to 35 U.S.C. §371, of International Patent Application No. PCT/JP2012/061097 filed on Apr. 25, 2012, which claims priority to application no. JP 2011-097377 filed in Japan on Apr. 25, 2011.

REFERENCE TO SEQUENCE LISTING

A Sequence Listing is submitted herewith, pursuant to 37 C.F.R. 1.821(c), as an ASCII compliant text file named "SeqList.txt", which was created on Sep. 10, 2013 and has a size of 17 kilobytes. The contents of the aforementioned "SeqList.txt" file are hereby incorporated by reference and in their entirety.

TECHNICAL FIELD

The present invention relates to a method for detecting or diagnosing a neurological disease associated with cognitive impairment by measuring the extracellular domain of EphA4, and a detection or diagnostic kit for this purpose.

BACKGROUND ART

Eph receptor A4 (EphA4) is a member of the receptor tyrosine kinase family and is a molecule regulating post-synaptic morphogenesis. It is known that knockout of EphA4 or expression of an EphA4 dominant-negative mutant causes a reduction in the number of spines, which are small thorn-like protrusions found on dendrites, and also makes their shape slender (Non-patent Document 1). It is generally proposed that the processes of memory and learning are reflected in the number and/or morphology of spines.

Recent studies have clarified that this EphA4 undergoes γ-secretase-mediated cleavage and the cleaved intracellular fragment activates a small GTP-binding protein, Rac, to thereby stimulate spine formation (Patent Documents 1 and 2, and Non-patent Document 2). During the above γ-secretase-mediated cleavage process, full-length EphA4 is first cleaved by another type of protease (MMP (matrix metalloproteinase) family) different from γ-secretase to separate the extracellular domain of EphA4. The region remaining on the cell membrane after MMP-mediated cleavage is then cleaved by γ-secretase. Moreover, it is known that MMP-mediated cleavage of the EphA4 extracellular domain is induced in a neuronal activity-dependent manner (Non-patent Document 2), and it is also kwon that this cleavage reaction of the extracellular domain is a rate-limiting step in this series of cleavage processes.

However, it has not been clarified for what type of disease EphA4 or its extracellular domain serves as a marker.

PRIOR ART DOCUMENTS

Patent Documents

Patent Document 1: WO2008/150010
Patent Document 2: WO2009/069808

Non-Patent Documents

Non-patent Document 1: Murai K K, Nguyen L N, Irie F, Yamaguchi Y, Pasquale E B. Control of hippocampal dendritic spine morphology through ephrin-A3/EphA4 signaling. Nat Neurosci. 2003 February; 6 (2): 153-60.

Non-patent Document 2: Inoue E, Deguchi-Tawarada M, Togawa A, Matsui C, Arita K, Katahira-Tayama S, Sato T, Yamauchi E, Oda Y, Takai Y. Synaptic activity prompts gamma-secretase-mediated cleavage of EphA4 and dendritic spine formation. J Cell Biol. 2009 May 4; 185 (3): 551-64.

SUMMARY OF THE INVENTION

Problem to be Solved by the Invention

The object of the present invention is to provide a method for detecting or diagnosing a neurological disease associated with cognitive impairment by using the extracellular domain of EphA4 as an indicator, and a kit for use in this detection or diagnosis.

Means to Solve the Problem

As a result of extensive and intensive efforts made to achieve the above object, the inventors of the present invention have found that EphA4 is reduced in patients with neurological diseases associated with cognitive impairment, e.g., Alzheimer's disease patients or mild cognitive impairment (MCI) patients before developing Alzheimer's disease. Based on this finding, the inventors of the present invention have further found that a neurological disease associated with cognitive impairment can be detected when using the extracellular domain of EphA4 as an indicator. These findings led to the completion of the present invention.

Namely, the present invention is as follows.

(1) A biomarker for a neurological disease associated with cognitive impairment, which comprises the extracellular domain of EphA4.

(2) The marker according to (1) above, wherein said EphA4 is a protein shown in (a) or (b) below:
(a) a protein which consists of the amino acid sequence shown in SEQ ID NO: 1 or 2; or
(b) a protein which consists of an amino acid sequence with deletion, substitution or addition of one or several amino acids in the amino acid sequence shown in SEQ ID NO: 1 or 2 and which serves as a substrate for matrix metalloproteinase or γ-secretase.

(3) A method for detecting a neurological disease associated with cognitive impairment, which comprises the following steps:
(a) contacting a biological sample taken from a subject with an antibody which binds to the extracellular domain of EphA4 to thereby measure the amount of the EphA4 extracellular domain; and
(b) determining the subject as suffering from or being at risk of suffering from a neurological disease associated with cognitive impairment if the amount of the EphA4 extracellular domain derived from the subject is lower than a control.

(4) A method for diagnosing a neurological disease associated with cognitive impairment, which comprises the following steps:
(a) contacting a biological sample taken from a subject with an antibody which binds to the extracellular domain of EphA4 to thereby measure the amount of the EphA4 extracellular domain; and (b) diagnosing the subject as suffering from or being at risk of suffering from a neurological disease associated with cognitive impairment if the amount of the EphA4 extracellular domain derived from the subject is lower than a control.
(5) The method according to (3) or (4) above, wherein the biological sample is a body fluid.
(6) The method according to (5) above, wherein the body fluid is at least one selected from the group consisting of blood, serum, plasma, blood cells, urine, spinal fluid, saliva, lacrimal fluid and sweat.
(7) The method according to any one of (3) to (6) above, wherein the amount of the EphA4 extracellular domain is measured by ELISA.
(8) The method according to any one of (3) to (7) above, wherein the neurological disease associated with cognitive impairment is a disease with reduced neuronal activity in glutamatergic neurons.
(9) The method according to any one of (3) to (8) above, wherein the neurological disease associated with cognitive impairment is Alzheimer's disease, mild cognitive impairment or frontotemporal dementia.
(10) A kit for detecting or diagnosing a neurological disease associated with cognitive impairment, which comprises an antibody which binds to the extracellular domain of EphA4.

Effects of the Invention

The present invention enables the detection of neurological diseases associated with cognitive impairment, such as Alzheimer's disease and mild cognitive impairment (MCI), by using a reduction in the extracellular domain of EphA4 as an indicator.

The present invention will be described in more detail below.

DESCRIPTION OF EMBODIMENTS

The present invention will be described in more detail below. The following embodiments are illustrated to describe the present invention, and it is not intended to limit the present invention only to these embodiments. The present invention can be implemented in various modes, without departing from the spirit of the present invention.

It should be noted that all publications cited herein, including prior art documents, patent gazettes and other patent documents, are incorporated herein by reference. Moreover, this specification incorporates the contents disclosed in the specification of Japanese Patent Application No. 2011-097377 (filed on Apr. 25, 2011), based on which the present application claims priority.

The present invention is directed to a method in which the extracellular domain of EphA4 is used as an indicator (biomarker) for detection or diagnosis of neurological diseases associated with cognitive impairment. This method has now been completed based on the finding that the extracellular domain of EphA4 is reduced in patients with neurological diseases associated with cognitive impairment (e.g., Alzheimer's disease, mild cognitive impairment or frontotemporal dementia) when compared to normal subjects.

As used herein, the term "EphA4" refers to a known polypeptide serving as a regulatory factor for synapse formation and/or maintenance (Murai K K et al., Nat Neurosci. 2003 February; 6 (2):153-60). EphA4 is structured to comprise an MMP cleavage site, a γ-secretase cleavage site, a transmembrane domain and a kinase active site, and its ligand is among the Ephrin A family (Aoto, J et al., Brain Res. 2006 11).

As used herein, the term "extracellular domain" refers to an N-terminal fragment of EphA4, which will be released into the extracellular environment upon MMP-mediated cleavage. The extracellular domain of EphA4 is also referred herein as the "EphA4 extracellular domain."

As used herein, the term "fragment of the intracellular region" refers to a cleavage product of EphA4 after MMP-mediated cleavage, i.e., a C-terminal fragment of EphA4 which is not the extracellular domain. Such a fragment of the intracellular region includes a transmembrane domain and an intracellular domain, and it serves as a substrate for γ-secretase. A subfragment released into cells from the fragment of the intracellular region upon γ-secretase-mediated cleavage is referred to as an EphA4 intracellular domain (EICD).

Figure 1:
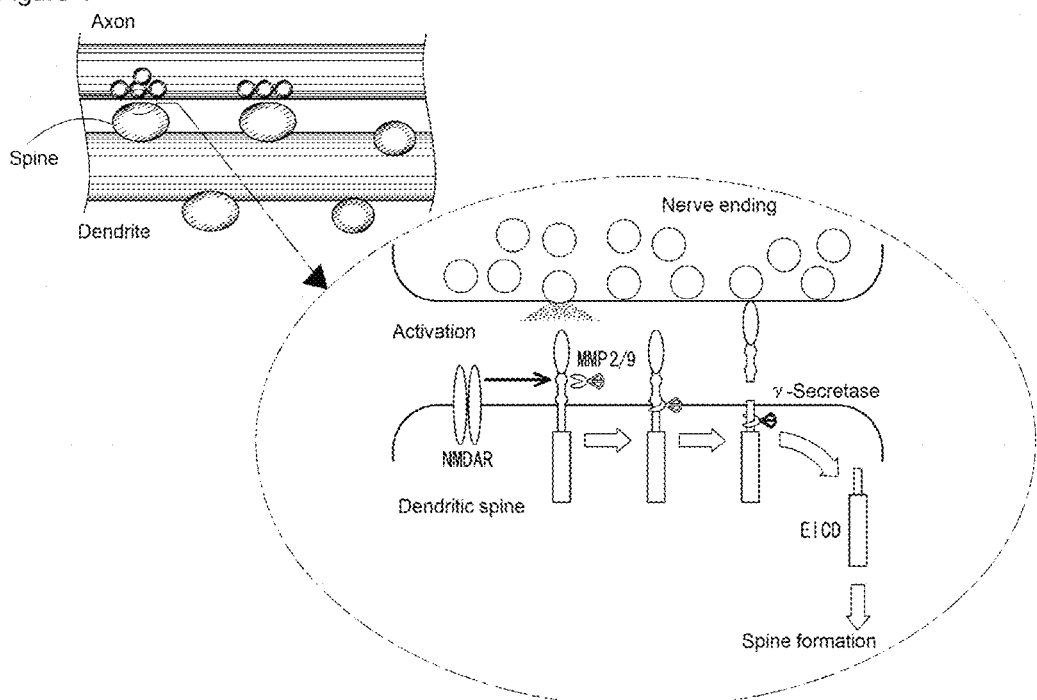
FIG. 1 schematically shows the cleavage process (processing pathway) of EphA4.

The cleavage process (processing pathway) of EphA4 is schematically shown in FIG. 1.

As shown in FIG. 1, once neuronal activity has occurred and neurotransmitters have acted on the NMDA receptor (NMDAR), which is a glutamate receptor, MMP (matrix metalloproteinase)-mediated EphA4 cleavage reaction will be induced to cleave EphA4 into a fragment of the extracellular region released into the extracellular environment (i.e., the extracellular domain) and a fragment of the intracellular region remaining within the membrane and cell (i.e., a fragment including the transmembrane domain and the intracellular domain). After MMP-mediated cleavage, the fragment of the intracellular region will further be cleaved by γ-secretase and released as an intracellular domain (i.e., EICD) (released into the cell).

In subjects without cognitive impairment, including normal subjects, EphA4 cleavage reaction will proceed by the action of MMP and γ-secretase, so that the extracellular domain and EICD will be cleaved and released from EphA4. On the other hand, in patients with neurological diseases associated with cognitive impairment, the extracellular domain is less likely to be cleaved and released or is not cleaved and released due to their reduced neurological functions. Since the MMP-cleaved EphA4 extracellular domain is released into the extracellular environment, it is possible to detect or diagnose a neurological disease associated with cognitive impairment when the amount of this domain is measured in a subject.

Namely, the presence of the EphA4 extracellular domain is indicative of the absence of cognitive impairment, while the absence of the EphA4 extracellular domain or its reduction in comparison with a control is indicative of the presence of a neurological disease associated with cognitive impairment.

The inventors of the present invention have found, ahead of others, that a neurological disease associated with cognitive impairment can be detected or diagnosed when the amount of the EphA4 extracellular domain is measured using a specific antibody which binds to the EphA4 extracellular domain.

Namely, the inventors of the present invention have demonstrated that the EphA4 extracellular domain in a subject serves as a biological indicator for neurological diseases associated with cognitive impairment and can be used as a biomarker. Based on this finding, the inventors have demonstrated that the amount of the EphA4 extracellular domain in a subject can serve as a biological indicator for neurological diseases associated with cognitive impairment.

Thus, the present invention enables the determination of whether or not a subject has a neurological disease associated with cognitive impairment by measuring the amount of the EphA4 extracellular domain derived from the subject.

The present invention provides a method for detecting or diagnosing a neurological disease associated with cognitive impairment using the extracellular domain of EphA4, which comprises the step of measuring the amount of the EphA4 extracellular domain from a biological sample taken from a subject. This detection step may be accomplished as shown in (a) and (b) below, by way of example:

(a) contacting a biological sample derived from a subject with an antibody which binds to the EphA4 extracellular domain to thereby measure the amount of the EphA4 extracellular domain; and (b) allowing the amount of the EphA4 extracellular domain to be correlated with a neurological disease associated with cognitive impairment.

The result thus obtained is used as a biological indicator for determining whether the subject suffers from or is at a high risk of suffering from a neurological disease associated with cognitive impairment. In the detection and diagnosis methods of the present invention, the amount of the EphA4 extracellular domain is correlated with a neurological disease associated with cognitive impairment on the basis of the following criteria.

If the amount of the EphA4 extracellular domain derived from a subject is lower than a control (e.g., the amount of the EphA4 extracellular domain derived from normal subjects and/or Parkinson's disease patients), the subject is determined or diagnosed as suffering from or being at a high risk of suffering from a neurological disease associated with cognitive impairment. The control may include the amount of the EphA4 extracellular domain derived from patients with various neurological diseases as long as they are free from cognitive impairment, but it is preferably the amount of the EphA4 extracellular domain derived from normal subjects and/or Parkinson's disease patients, and more preferably the amount of the EphA4 extracellular domain derived from normal subjects. It should be noted that cases where the amount of the EphA4 extracellular domain derived from a subject is lower than the control also include those where the amount of the EphA4 extracellular domain derived from a subject is below the detection limit.

As used herein, the term "amount" refers to the absolute or relative amount of EphA4 in a sample, which can be expressed as a concentration or may be simply expressed as whether or not EphA4 is present, i.e., expressed as the presence or absence of EphA4. The term "contact" is intended to mean that the EphA4 extracellular domain and an antibody which binds to the EphA4 extracellular domain are placed in an environment where they can be reacted with each other under given conditions, as exemplified by mixing of the above antibody into a sample containing the EphA4 extracellular domain, adding the above sample to a reaction system containing the antibody, etc.

When the EphA4 extracellular domain is contacted with the antibody which binds to the EphA4 extracellular domain, the anti-EphA4 extracellular domain antibody will bind to the EphA4 extracellular domain via antigen-antibody reaction. In the case of a reaction system using a biological sample derived from a normal subject or a biological sample derived from a patient without cognitive impairment (e.g., a patient with Parkinson's disease), cleavage reaction occurs on EphA4 to thereby cleave and release the EphA4 extracellular domain. In contrast, in a reaction system using a biological sample derived from a patient with a neurological disease associated with cognitive impairment, little or no cleavage reaction occurs on EphA4, so that the amount of the EphA4 extracellular domain is low. When such a reaction system using a biological sample derived from a normal subject or a biological sample derived from a patient without cognitive impairment (e.g., a patient with Parkinson's disease) is used as a control, a subject can be assessed as suffering from or being at risk of suffering from a neurological disease associated with cognitive impairment if the EphA4 extracellular domain derived from the subject is lower than the control. For this reason, the EphA4 extracellular domain can be used as a biomarker for neurological diseases associated with cognitive impairment.

Examples of "EphA4" intended in the present invention include human EphA4 (NM_004438.3, NP_004429.1, BAG35298.1 (SEQ ID NO: 1), BC026327 (SEQ ID NO: 2), and so on.

In a preferred embodiment of the present invention, EphA4 is human EphA4, for example, a polypeptide comprising the amino acid sequence shown in SEQ ID NO: 1 or 2.

In the present invention, the EphA4 extracellular domain which serves as a biomarker for neurological diseases associated with cognitive impairment is preferably in its full-length form, but a partial sequence thereof or a mutated sequence thereof may also be possible. A mutant of EphA4 may be a polypeptide substantially functionally equivalent to EphA4, which comprises an amino acid sequence with deletion, substitution, insertion and/or addition of one or more (preferably one or several) amino acids in the full-length or partial sequence of EphA4 or with any combination of these modifications. Such a "polypeptide substantially functionally equivalent to EphA4" is intended to mean a polypeptide having the activity of EphA4, such as MMP- or γ-secretase-dependent cleavage activity, i.e., a peptide serving as a substrate for matrix metalloproteinase or γ-secretase.

As used herein, the term "substitution" is preferably intended to mean conservative substitution, in which one or more (preferably one or several) amino acid residues are replaced with other chemically similar amino acid residues such that the activity of the resulting polypeptide is not substantially altered. Examples include cases where one hydrophobic residue is replaced with another hydrophobic residue and where one polar residue is replaced with another polar residue having the same charge. For each amino acid, its functionally similar amino acids allowing such substitution are known in the art. More specifically, examples of non-polar (hydrophobic) amino acids include alanine, valine, isoleucine, leucine, proline, tryptophan, phenylalanine, methionine and so on. Examples of polar (neutral) amino acids include glycine, serine, threonine, tyrosine, glutamine, asparagine, cysteine and so on. Examples of positively charged (basic) amino acids include arginine, histidine, lysine and so on. Likewise, examples of negatively charged (acidic) amino acids include aspartic acid, glutamic acid and so on.

The number of amino acids which may be deleted, substituted, inserted and/or added as described above is, e.g., 1 to 30, preferably 1 to 20, more preferably 1 to 10, even more preferably 1 to 5, and particularly preferably 1 or 2.

Mutated amino acid sequences of EphA4 include amino acid sequences each sharing a homology of preferably 80% or more, more preferably 85% or more, even more preferably 90% or more, still even more preferably 95% or more, particularly preferably 98% or more, and most preferably 99% or more with the amino acid sequence of the wild-type polypeptide. Polypeptides comprising amino acid sequences each having the above homology fall within mutated polypeptides to be used in the present invention, as long as they have substantially the same activity as EphA4, e.g., the activity to receive MMP-mediated or γ-secretase-mediated cleavage (i.e., the activity to serve as a substrate for MMP or γ-secretase). Moreover, the above mutated polypeptides can be used as targets to be detected, as long as they have another activity, e.g., the activity to cause a morphological change in postsynapses, particularly to cause an Ephrin A-dependent morphological change, in addition to the above activity to serve as a substrate for MMP or γ-secretase. The activity to serve as a substrate for MMP or γ-secretase can be detected by ELISA or Western blotting, etc.

The above identity may be a numerical value calculated using any homology search program known to those skilled in the art, for example, may be calculated using default (initial setting) parameters in the homology algorithm BLAST (basic local alignment search tool) program of the National Center for Biotechnology Information (NCBI).

In the present invention, the EphA4 extracellular domain is preferably endogenous. In the case of endogenous EphA4 extracellular domain, any composition is possible as long as it contains the EphA4 extracellular domain derived from a part of a subject. Such a part of a subject may be, for example, a tissue, a cell, a cell membrane fraction or a purified membrane, each of which is derived from the above subject. Examples of such a cell include neuronal cells (e.g., cells in the central nervous system brain-derived neurons, cerebral cortex-derived neurons, cerebral cortex-derived primary cultured neurons, hippocampus-derived primary cultured neurons), glia cells and so on.

Moreover, in these cells, the EphA4 extracellular domain may remain in the state of being contained in a part of the subject or may be an EphA4 extracellular domain fraction of a cell lysate prepared from the subject. Such a cell lysate may be prepared from EphA4-containing cells, e.g., by lysis with a hypotonic solution or a surfactant or by ultrasonic or physical homogenization, optionally followed by treatment with a purification means such as a column.

For analysis of EphA4 cleavage, an antibody which binds to the full-length EphA4 may be used, but it is necessary to use an antibody which recognizes the EphA4 extracellular domain, because the amount of the EphA4 extracellular domain (N-terminal fragment) should be measured.

The EphA4 extracellular domain may be quantified by measuring signals generated when the labeled antibody binds to the EphA4 extracellular domain.

Examples of the above label include biotin labels, enzyme labels, radioactive labels, fluorescent labels, chemiluminescent labels and so on. Moreover, modifications may also be made to integrate any detectable moiety in addition to the label. In the present invention, the antibody for use in analysis of EphA4 cleavage may be provided with one or two or more of these labels or modifications.

The antibody for use in analysis of EphA4 cleavage may be an antibody against EphA4 and is not limited in any way as long as it is an antibody which recognizes EphA4, as exemplified by an antibody which recognizes the EphA4 extracellular domain.

Those skilled in the art would be able to prepare such an antibody by immunization with an immunogen (antigen) in accordance with existing standard procedures for monoclonal antibody preparation. For example, the antigen is immunized into a non-human mammal, optionally together with Freund's adjuvant. Polyclonal antibodies can be obtained from the serum taken from the immunized animal. On the other hand, monoclonal antibodies are prepared as follows: antibody-producing cells obtained from the immunized animal and myeloma cells having no ability to produce autoantibodies are used to prepare fused cells (hybridomas), and these hybridomas are cloned and screened to select clones which produce monoclonal antibodies having specific affinity to the antigen used for immunization of the mammal Production of monoclonal antibodies from hybridomas may be accomplished by culturing the hybridomas in vitro or in vivo (e.g., in the peritoneal fluid of non-human mammals, preferably mice or rats, more preferably mice) and then isolating monoclonal antibodies from the resulting culture supernatant or the peritoneal fluid of the mammals. For isolation and purification of monoclonal antibodies, the above culture supernatant or peritoneal fluid may be subjected to saturated ammonium sulfate, euglobulin precipitation, caproic acid method, caprylic acid method, ion exchange chromatography (e.g., DEAE or DE52), affinity column chromatography on an anti-immunoglobulin column or a Protein A column, etc. These monoclonal antibodies also encompass those consisting of heavy chains and/or light chains having amino acid sequences with deletion, substitution or addition of one or several amino acids in the amino acid sequences of the heavy chains and/or light chains constituting the original antibodies.

In the present invention, it is possible to use anti-human EphA4 monoclonal antibody No. 8 (i.e., a monoclonal antibody which binds to the EphA4 extracellular domain) and so on, as shown in the Example section below.

In the present invention, the EphA4 extracellular domain can be used as a clinical biomarker for neurological diseases associated with cognitive impairment. By measuring the amount of the EphA4 extracellular domain in a biological sample, a neurological disease associated with cognitive impairment can be detected on the basis of the measured results.

<Biological Sample>

The biological sample is not limited in any way and examples include liquid components derived from the living body (also collectively referred to as body fluid) such as blood and blood components (e.g., serum, plasma, blood cells), urine, spinal fluid, saliva, lacrimal fluid, sweat and so on, as well as solid components derived from the living body such as hair, tissue pieces excised by biopsy, etc. Preferred is blood or a blood component, and particularly preferred is serum or plasma. It should be noted that a sample taken from the living body may be used directly or further subjected to some kind of treatment for use as a biological sample in the present invention.

<Measurement of the Amount of the EphA4 Extracellular Domain>

The amount of the EphA4 extracellular domain may be measured by any technique as long as it has sufficient detection sensitivity and measurement accuracy, and known analysis techniques may be used for this purpose. Examples of analysis techniques include immunological assays such as ELISA (enzyme-linked immunosorbent assay), RIA (radioimmunoassay), sandwich ELISA, immuno-complex transfer (ICT), antibody PCR (immuno-PCR), EIA (enzyme immuno assay), CLIA (chemiluminescent immuno assay), ECLIA (electrochemiluminescence immuno assay), FIA (fluorescent immuno assay) and so on, as well as surface plasmon resonance such as biacore. Moreover, known analysis techniques and immunological assays may be used in combination for measurement. In this case, preferred is a combination of ICT and another immunological assay, as exemplified by ICT-ELISA, ICT-CLIA, ICT-immuno-PCR, ICT-EIA, ICT-RIA, ICT-ECLIA, ICT-FIA, etc.

Preferred neurological diseases associated with cognitive impairment to be detected in the present invention may be, for example, diseases with reduced neuronal activity in glutamatergic neurons. The phrase "with reduced neuronal activity in glutamatergic neurons" is intended to mean a reduced amount of glutamic acid released from the nerve endings of glutamatergic neurons or reduced functions of neuronal glutamate receptors projected from glutamatergic neurons. Confirmation of whether or not the neuronal activity in glutamatergic neurons is reduced may be accomplished by detecting changes in the amount of EphA4 cleaved in a neuronal activity-dependent manner. Particularly preferred neurological diseases associated with cognitive impairment include, for example, Alzheimer's disease, mild cognitive impairment (MIC) or frontotemporal dementia (Pick's disease), etc.

The mean value of EphA4 extracellular domain levels is about 0.1 ng/mL plasma in normal subjects. In contrast, among patients with neurological diseases associated with cognitive impairment, Alzheimer's disease (AD) patients often are at about half level or less of normal subjects's concentration ($P<0.01$), which is almost impossible to detect (below the detection limit). Mild cognitive impairment (MCI) patients also often are at about half level or less of the mean value in normal subjects's concentration (0.1 ng/mL) ($P<0.05$), which is below the detection limit. Thus, in the present invention, the above mean value can be used as a standard for detection or diagnosis of a neurological disease associated with cognitive impairment.

In the method of the present invention, biological tissue samples derived from a plurality of subjects may be used in some cases for measurement of EphA4 extracellular domain levels. Thus, in the predetermined number of patients with neurological diseases associated with cognitive impairment (primary population), the amount of the EphA4 extracellular domain may be measured and processed by statistical analysis or the like for comparison with the control. Moreover, the resulting measured values may be used as basic data, and a comparison may be made between these basic data and the amount of the EphA4 extracellular domain in a biological sample or samples taken from a subject or subjects to be detected.

Further, if the above measured data of the subjects fall within the predetermined range of values, they may be incorporated into the values of the above population and subjected again to data processing (e.g., data averaging) of EphA4 extracellular domain levels to increase the number of cases of target patients (population). The increased number of cases can improve the accuracy of detection or diagnosis of a neurological disease associated with cognitive impairment.

<Kit>

In the present invention, the EphA4 extracellular domain serves as a marker for neurological diseases associated with cognitive impairment. Thus, an antibody which binds to the EphA4 extracellular domain can be used as an assay kit designed for in vitro experiments or for patients with neurological diseases associated with cognitive impairment. In this case, the present invention can be configured in the form of a kit comprising an antibody which binds to the EphA4 extracellular domain or at least one member selected from a buffer, a cell culture medium, an antibody which binds to the EphA4 extracellular domain, a fluorescent dye and so on. Such a kit may also comprise an instruction manual which describes, e.g., test procedures for binding assay between anti-EphA4 extracellular domain antibody and EphA4 extracellular domain.

The kit of the present invention may comprise tools for use in ELISA, immunoblotting and/or Western blotting techniques (e.g., reaction container, blotting membrane), reagents (e.g., buffer, culture medium), an instruction manual, etc.

EXAMPLES

The present invention will be further described in more detail by way of the following examples, which are not intended to limit the scope of the present invention.

Example 1

<Measurement of EphA4 Extracellular Domain Concentration>
~ELISA-Based Measurement~

Anti-human EphA4 extracellular domain monoclonal antibody No. 8 (Eisai Co., Ltd., Japan) was purified and adjusted with 50 mM Tris/HCl (pH 7.5) to a concentration of 5 µg/ml, and then injected at 100 µl/well in a Maxisorp cup (NUNC). The cup was placed in a humid box and coated overnight at 4° C. After the antibody solution was removed by aspiration, a blocking solution (5% skimmed milk (Morinaga Milk Industry Co., Ltd., Japan), 50 mM Tris/HCl (pH 7.5), 150 mM NaCl, 0.1% sodium azide) was injected at 200 µl/well, followed by blocking at room temperature for 2 hours or at 4° C. for one day or more (hereinafter referred to as "No. 8 cup"). Anti-human EphA4 extracellular domain monoclonal antibody No. 9 (Eisai Co., Ltd., Japan) was labeled with peroxidase using a Peroxidase Labeling Kit-$NH_2$ (DOJINDO MOLECULAR TECHNOLOGIES, Inc.) in accordance with the instruction manual attached to the kit (hereinafter referred to as "peroxidase-labeled No. 9 antibody").

The No. 8 cup was washed three times with a washing solution (50 mM Tris/HCl (pH 7.5), 150 mM NaCl, 0.01% Tween 20), and a sample which had been diluted 5-fold with an analyte diluent (5% skimmed milk (Morinaga Milk Industry Co., Ltd., Japan), 50 mM Tris/HCl (pH 7.5), 150 mM NaCl, 0.2% EDTA·3Na, 4% polyethylene glycol 6000, 0.1% sodium azide) was injected at 100 µl/well and reacted at room temperature for 2 hours. After washing three times with the washing solution, the peroxidase-labeled No. 9 antibody which had been diluted 1500-fold with a labeled antibody diluent (5% skimmed milk (Morinaga Milk Industry Co., Ltd., Japan), 50 mM Tris/HCl (pH 7.5), 150 mM NaCl, 0.2% EDTA·3Na, 4% polyethylene glycol 6000, 0.2% ProClin 150 (SUPELCO, 49376-U)) was injected at 100 µl/well and reacted at room temperature for 1 hour. After washing three times with the washing solution, a 3,3',5,5'-Tetramethylbenzidine (TMB) Liquid Substrate System for ELISA (SIGMA) was injected at 100 µl/well and reacted at room temperature for 30 minutes. 0.5 M $H_2SO_4$ was injected at 100 µl/well to stop the reaction, and OD (450 to 650 nm) was then measured for each well. The purified recombinant human EphA4 (Eisai Co., Ltd., Japan) was used as a standard to calculate the EphA4 concentration.

Figure 2:
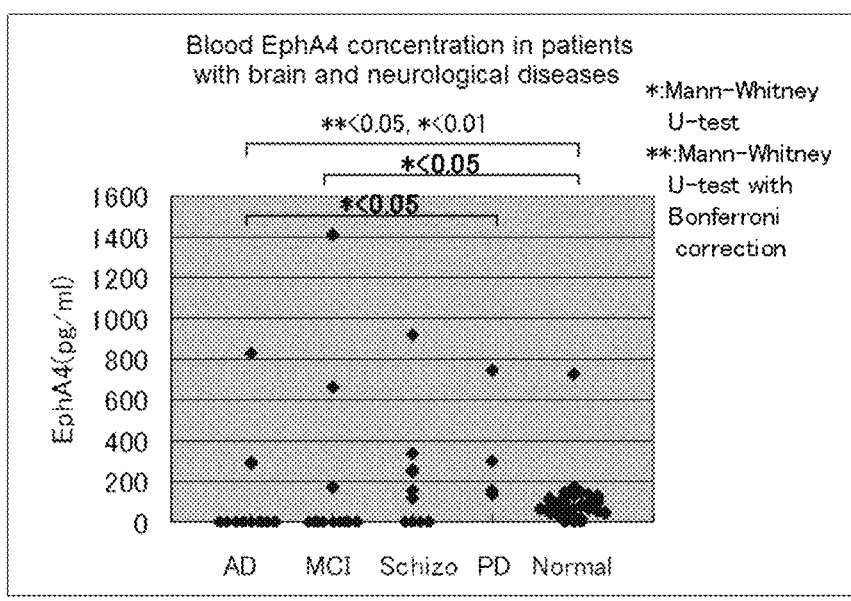
FIG. 2 shows a distribution of the measured values obtained by ELISA for the concentration of EphA4 extracellular domain in plasma analytes.

FIG. 2 shows the results measured for the plasma analytes obtained from 10 cases of Alzheimer's disease patients (AD), 10 cases of mild cognitive impairment patients (MCI), 10 cases of schizophrenia patients (Schizophrenia), 4 cases of Parkinson's disease patients (PD) and 36 cases of normal subjects (Normal).

The EphA4 concentration was below the detection limit in 8 of the 10 AD cases, 7 of the 10 MCI cases, 4 of the 10 schizophrenia cases, 0 of the 4 PD cases, and 3 of the 36 normal cases. The cases below the detection limit were statistically analyzed by using a provisional value below the detection limit, indicating that AD showed a significantly lower value than Normal at a significance level of less than 1% and also showed a significantly lower value than PD at a significance level of less than 5% in the Mann-Whitney U-test. Likewise, MCI also showed a significantly lower value than Normal at a significance level of less than 5%.

INDUSTRIAL APPLICABILITY

The present invention enables the detection of neurological diseases associated with cognitive impairment by using the EphA4 extracellular domain as a biological indicator (biomarker).

The invention claimed is:

1. A method for measuring the presence or amount of the EphA4 extracellular domain, comprising:
   (a) providing a body fluid taken from a subject having or suspected of having Alzheimer's disease or mild cognitive impairment;
   (b) contacting the body fluid with an antibody that specifically binds to the extracellular domain of EphA4; and
   (c) measuring the presence or amount of the EphA4 extracellular domain in the body fluid.

2. The method according to claim 1, wherein the body fluid is at least one selected from the group consisting of blood, serum, plasma, urine, spinal fluid, saliva, lacrimal fluid and sweat.

3. The method according to claim 1, wherein the body fluid is serum or plasma.

4. The method according to claim 1, wherein the presence or amount of the EphA4 extracellular domain is measured by ELISA.

* * * * *